US00PP10744P

United States Patent [19]

Nicolai

[11] Patent Number: Plant 10,744

[45] Date of Patent: Jan. 5, 1999

[54] APPLE TREE NAMED 'M9-RN19'

[75] Inventor: René Nicolai, Alken, Belgium

[73] Assignee: Rene Nicolai N.V. Fruitboomwekerij, Belgium

[21] Appl. No.: 996,506

[22] Filed: Dec. 23, 1992

Related U.S. Application Data

[63] Continuation of Ser. No. 642,993, Jan. 18, 1991, abandoned.

[51] Int. Cl.[6] ..... A01H 5/00

[52] U.S. Cl. ..... Plt./34.1

[58] Field of Search ..... Plt./34.1, 35, 35.1, Plt./35.2

[56] References Cited

PUBLICATIONS

Anon., *Stark Bro's Fruit Tree Catalog & Guide for the Professional Grower* 1989 Stark Bro's Nursery and Orchards Co., Louisana, Mo. pp. 18 and 19.

Anon, Oregon Rootstock Inc. Catalog, 1985, Oregon Rootstock, Inc., Woodburn, Oregon. pp. 8–15.

Tukey, H.B. "7 Dwarfing Rootstocks for Apple Trees"0 *Dwarfed Fruit Trees.* The Macmillan Co., N.Y. 1964 pp. 123–154.

van Oosten, H.J., et al., "Differences between Subvarieties of 'M.9'" *De–Fruitteelt* (all 1984) No. 32, pp. 924–926; No. 33, pp. 950–951 No. 34, pp. 968–969; and No. 35 pp. 988–989 *(English Translations provided only).

Masseron, A., "Study and Selection of Paradise Jaine De Metz Rootstock of the Apple Tree" Interprofessional Technical Center for the Fruits and Vegetables, CTIFL, Service for Improving Production, Domaine de Lanxade, Prigonrieux 24130 La Force, pp. 35–57 (with pages missing in between) *(English Translations provided only).

Ziebig, R., et al., Autonomous Province Bozen–South Tyrol, Division I Agriculture and Forestry. 1992 Activity Program for the Agriculture and Forestry Experimental Center. *(English Translations provided only).

*Primary Examiner*—Howard J. Locker

*Attorney, Agent, or Firm*—Chernoff, Vilhauer, McClung & Stenzel, LLP

[57] ABSTRACT

This invention relates to a new and distinct apple tree rootstock clone that originated as a mutation of Malling 9 (M9). Standard growing apple cultivars propagated on this new rootstock are approximately 65% of the size of like apple trees growing on apple seedling rootstocks. Compared to its M9 parent, this new clone produces many more and larger lateral branches, has leaves with acute tips and has more sinuate serrations. The clone is also more vigorous and produces a larger number of rooted plants in a given area of stoolbed.

7 Drawing Sheets

BACKGROUND AND SUMMARY OF THE INVENTION

The inventor of the subject variety, Rene Nicolai, was the owner of Rene Nicolai Nursery, which propagated and sold Malling Nine (M9) apple tree root stock. Root stock are propagated by placing plants in a stool bed which encourages root growth and then dividing the resulting roots into individual plants. Over the years Mr. Nicolai searched the M9 stool beds for M9 mutants which were superior to the parent variety in those characteristics which are desirable for apple tree root stock.

The subject clone was selected in 1967 from a large stool bed of M9 plants that was planted in 1960 at the Rene Nicolai Nursery at Linderstoot, 22-B-3820 Alken, Belgium. The original source of the plants in the bed was the East Malling Research Station in England. Following its selection, the clone was assigned a number (RN19) and was propagated for further testing and evaluation.

Since all original M9 root stocks have been found to be virus infected, the RN19 plants were subsequently heat treated by application of dry heat, in order to obtain virus-free testing, the new root stock cone was again exposed to multiplication techniques (stooling) followed by continued testing and evaluation.

Virus-free RN19 progeny plants were expanded into small stool bed plantings at several locations which were planted separately in order to examine the new variety's individual characteristics in small semi-commercial stool bed sites. Since 1974 nearly 40,000 plants of the subject variety have been planted at the following six sites and, in the process, may generations of the tree have been produced.

1. A site at Deveaux, Belgium was planted in the spring of 1974 with 1,500 plants of the subject clone.

2. A site at Bordeaux, France was planted in 1977 with 200 plants of the subject clone.

3. A site at Wissenhoeve, Belgium was planted in the spring of 1980 with 2,058 plants of the subject clone.

4. A site near St. Truiden, Belgium was planted in the spring of 1982 with 100 plants of the subject clone. 5. A site at Henkaenrts, Belgium was planted in the spring of 1986 with 3,250 plants of the subject clone.

6. A site at Ephrata, Wash. was planted in the spring of 1990 with 2,000 plants of the subject clone.

Clone RN19 was subsequently finally selected as a rootstock clone that continues to possess growth and rooting characteristics that are distinctly different from its M9 parent.

It distinguished itself in these beds from its M9 parent in the following ways:

1. The subject clone produces many more lateral limbs (feathers or spurs) than its M9 parent and grows more robustly in the stoolbed (FIGS. 1 and 2; Charts 1 and 2). The average increase in height of daughter plants growing in the stoolbed is approximately 20% (FIG. 6, M 9; and FIG. 7, RN19) and the average increase in the number of feathers produced is approximately three-fold at Bordeaux, France and almost six-fold at Ephrata, Wash. (Charts 1 and 2). A significant difference in the average length of the individual feathers produced is also noted (Chart 2). Because of RN19's more robust growth and its characteristic habit of producing more and larger feathers, an increased difference in the average number of leaves produced per daughter plant also occurs (Chart 2). A slight increases difference in the average number of nodes per shoot and in the average stem circumference is also noted (Chart 2). RN19 exhibits a much lesser early bloom characteristic than does its M 9 parent (Chart 3). Leaf size (adding the length and width together) and the length of the leaf particles are consistently smaller than the virus-free M 9 (Chart 4).

CHART 1

Percent of Layer Plants with Side Limbs (Feathers)
(Test Stooling Beds at Bordeaux, France)

| Rootstock | Year | | | | |
|---|---|---|---|---|---|
| Clone | 79/80 | 80/81 | 81/82 | 82/83 | Average |
| M9 (virus-free) | 13 | 8 | 25 | 0 | 11.4 |
| RN8 | 8 | 6 | 13 | 0 | 6.8 |
| RN19 | 41 | 32 | 44 | 19 | 34.0 |
| RN29 | 39 | 22 | 35 | 15 | 27.8 |

CHART 2

Growth Characteristics
(Test Stooling Beds at Ephrata, Washington)

| Rootstock Clone | Length of Shoot (cm) | Number of Nodes/ Shoot | Number of Spurs/ Shoot | Length of Spur (cm) | Number of Leaves/ Shoots | Circum-ference of Stem (cm) |
|---|---|---|---|---|---|---|
| M9 | 66.80* | 39.20 | 3.00 | 1.50 | 53.00 | 3.24 |
| RN8 | 62.10 | 42.10 | 1.80 | 1.20 | 57.20 | 3.80 |
| RN19 | 78.20 | 41.00 | 18.60 | 8.60 | 88.30 | 3.51 |
| RN29 | 86.20 | 45.60 | 21.40 | 10.30 | 100.00 | 3.54 |

*All numbers shown are the average of 100 plants selected at random.

CHART 3

Bloom Characteristics
(Research Station at Gorsum, Belgium - 1985)

| Rootstock Clone | % of Rootstocks With Bloom (1 Year From Stoolbed) |
|---|---|
| RN8 | 29 |
| RN19 | 4 |
| RN29 | 0 |
| M9 (virus-free) | 15 |

CHART 4

Leaf Size and Respetive Petiole
Length of Respective Rootstock
(Test Stooling Beds at Bordeaux, France)

| Rootstock Clone | Length, L (mm) | Width, W (mm) | L + W (mm) | Length of Petiole |
|---|---|---|---|---|
| M9 (virus-free) | 101.7 | 63.8 | 165.5 | 32.5 |
| RN8 | 98.8 | 73.6 | 172.4 | 34.0 |
| RN19 | 91.4 | 60.0 | 151.4 | 30.8 |
| RN29 | 85.5 | 57.1 | 142.6 | 28.5 |

2. The subject clone has the ability to produce many more rooted daughter plants per mother plant and per meter of stoolbed row than its M 9 parent (FIGS. 4 and 5; Charts 5, 6 and 7). Data collected at the Bordeaux test site in France shows an approximately three-fold increase in the number of daughter plants produced over a four-year period and data collected at the Deveaux test site in Belgium shows an approximately two-fold increase over six- and nine-year periods.

CHART 5

RN19 Stoolbed Production (Deveaux, Belgium)
No. Mother Plants - 555
Length of Bed (m) - 185

| Year | 82/83 | 83/84 | 84/85 | 85/86 | 86/87 |
|---|---|---|---|---|---|
| Grade (mm) | | | | | |
| 10/12 | 1,000 | 825 | 575 | 2,250 | 4,000 |
| 8/10 | 0 | 0 | 1,500 | 0 | 0 |
| 6/10 | 17,200 | 12,800 | 0 | 0 | 0 |
| 6/8 | 0 | 0 | 12,490 | 11,300 | 9,650 |
| 5/7 | 0 | 0 | 0 | 0 | 0 |
| 4/6 | 8,800 | 8,100 | 10,080 | 10,300 | 12,700 |
| 04 | 0 | 1,600 | 0 | 0 | 150 |
| #2s | 4,000 | 2,9400 | 2,700 | 2,000 | 5,300 |
| Totals | 31,000 | 26,225 | 27,345 | 25,850 | 31,800 |
| Per Mother Plant | 20.67 | 17.48 | 18.23 | 17.23 | 21.20 |
| Per Meter | 62.00 | 52.45 | 54.69 | 51.70 | 63.60 |

| Year | 87/88 | 88/89 | 89/90 | 90/91 | Average 82/91 |
|---|---|---|---|---|---|
| Grade (mm) | | | | | |
| 10/12 | 1,250 | 525 | 0 | 1,075 | |
| 8/10 | 4,225 | 4,500 | 3,900 | 5,150 | |
| 6/10 | 0 | 0 | 0 | 0 | |
| 6/8 | 9,950 | 8,000 | 9,050 | 3.100 | |
| 5/7 | 0 | 0 | 0 | 10,100 | |
| 4/6 | 9,500 | 6,700 | 10,500 | 2,600 | |
| 04 | 0 | 0 | 0 | 0 | |
| #2s | 5,700 | 3,000 | 10,500 | 2,600 | |
| Totals | 30,625 | 22,725 | 33,850 | 27,825 | |
| Per Mother Plant | 20.42 | 15.15 | 22.57 | 18.55 | 19.06 |
| Per Meter | 61.25 | 45.45 | 67.70 | 55.65 | 57.17 |

CHART 6

M9 (Virus-Free) Stoolbed Production (Deveaux, Belgium)
No. Mother Plants - 561
Length of Bed (m) - 187

| Year | 82/83 | 83/84 | 84/85 | 85/86 | 86/87 |
|---|---|---|---|---|---|
| Grade (mm) | | | | | |
| 10/12 | 225 | 100 | 250 | 750 | 464 |
| 8/10 | 0 | 0 | 450 | 0 | 0 |
| 6/10 | 4,150 | 2,950 | 0 | 2,350 | 2,200 |
| 6/8 | 0 | 0 | 3,400 | 0 | 0 |
| 5/7 | 0 | 0 | 0 | 0 | 0 |
| 4/6 | 1,800 | 1,600 | 2,200 | 1,600 | 3,000 |
| 04 | 0 | 300 | 0 | 0 | 0 |
| #2s | 700 | 800 | 500 | 500 | 1,400 |
| Totals | 6,875 | 5,750 | 6,800 | 5,200 | 7,064 |
| Per Mother Plant | 12.25 | 10.25 | 12.12 | 9.27 | 12.59 |
| Per Meter | 36.76 | 30.75 | 36.36 | 27.81 | 37.78 |

| Year | 87/88 | 88/89 | 89/90 | 90/91 | Average 82/91 |
|---|---|---|---|---|---|
| Grade (mm) | | | | | |
| 10/12 | 75 | — | — | — | |
| 8/10 | 450 | — | — | — | |
| 6/10 | 0 | — | — | — | |
| 6/8 | 2,700 | — | — | — | |

CHART 6-continued

| M9 (Virus-Free) Stoolbed Production (Deveaux, Belgium) No. Mother Plants - 561 Length of Bed (m) - 187 | | | | | |
|---|---|---|---|---|---|
| 5/7 | 0 | — | — | — | |
| 4/6 | 2,200 | — | — | — | |
| 04 | 0 | — | — | — | |
| #2s | 400 | — | — | — | |
| Totals | 5,825 | — | — | — | |
| Per Mother Plant | 10.38 | — | — | — | 11.14 |
| Per Meter | 31.15 | — | — | — | 33.43 |

CHART 7

Average Number of Plants Per Stoolbed Mother Plant (Test Stooling Beds at Bordeaux, France)

| | Year Planted and Age | | | | |
|---|---|---|---|---|---|
| Rootstock Clone | 79/80 2-Yr | 80/81 3-Yr | 81/82 4-Yr | 82/83 5-Yr | Average |
| M9 (virus-free) | 1.2 | 2.6 | .5 | 4.0 | 8.3 |
| RN8 | 2.1 | 3.9 | 3.8 | 6.4 | 16.2 |
| RN19 | 2.6 | 4.4 | 6.5 | 9.1 | 22.6 |
| RN29 | 4.4 | 5.6 | 5.7 | 11.3 | 27.0 |

3. Leaves of the subject clone are more acutely tipped and have sinuate serrations along their sides than leaves produced on its M 9 parent (FIG. 3). The average number of leaf serrations per centimeter of length was consistently less than those recorded on leaves of its M 9 parent (Chart 8).

CHART 8

Leaf Characteristics (Test Stooling Beds at Ephrata, Washington)

| Rootstock Clone | Number of Leaf Serrations per cm |
|---|---|
| M9 | 3.5** |
| RN19 | 2.7 |

*All numbers shown are the average of 200 leaves taken from 100 plants selected at random.

BRIEF DESCRIPTION OF THE DRAWINGS

Since the subject clone is intended to be used only as rootstock for apple cultivar, the drawings center on the vegetative parts rather than the flowers and fruits.

DESCRIPTION OF VEGETATIVE CHARACTERISTICS

Figure 1:
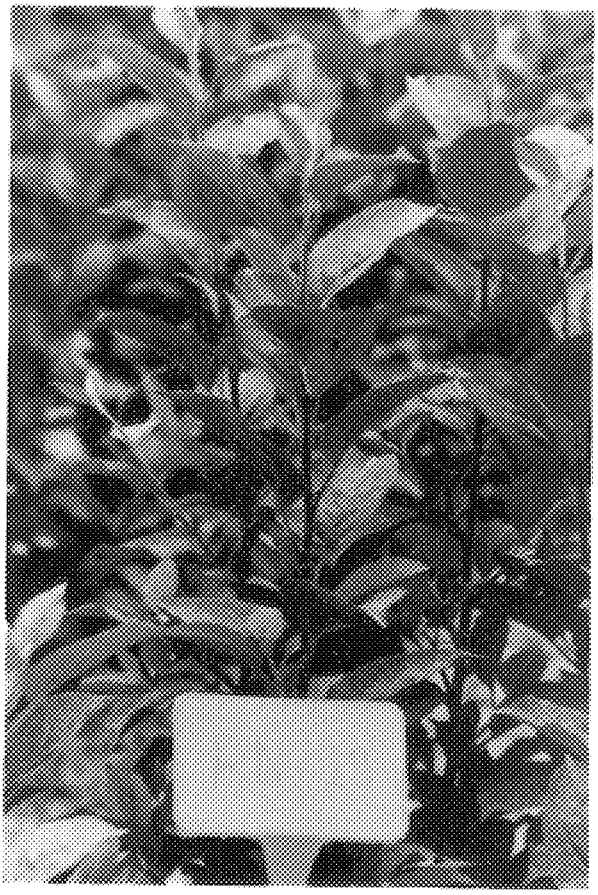
FIGS 1 and 2 show the few lateral branches on stoolbed plants.
Figure 2:
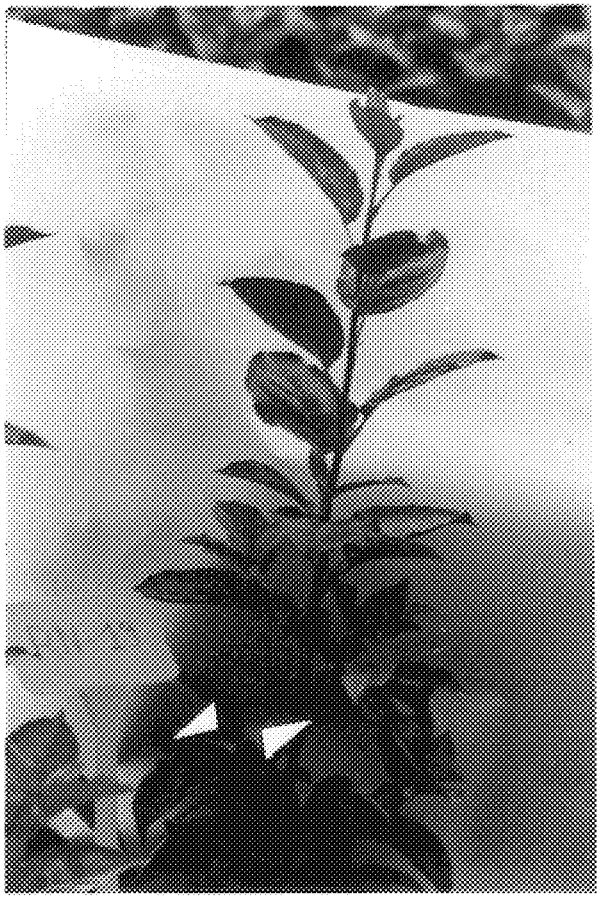
Figure 3:
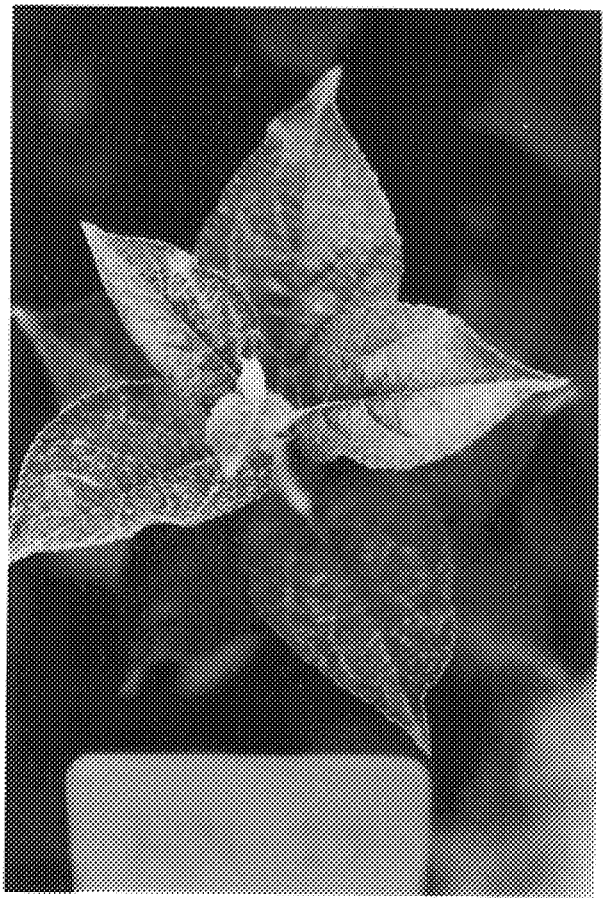
FIG. 3 shows acute tipped leaves and sinuate leafside serrations.
Figure 4:
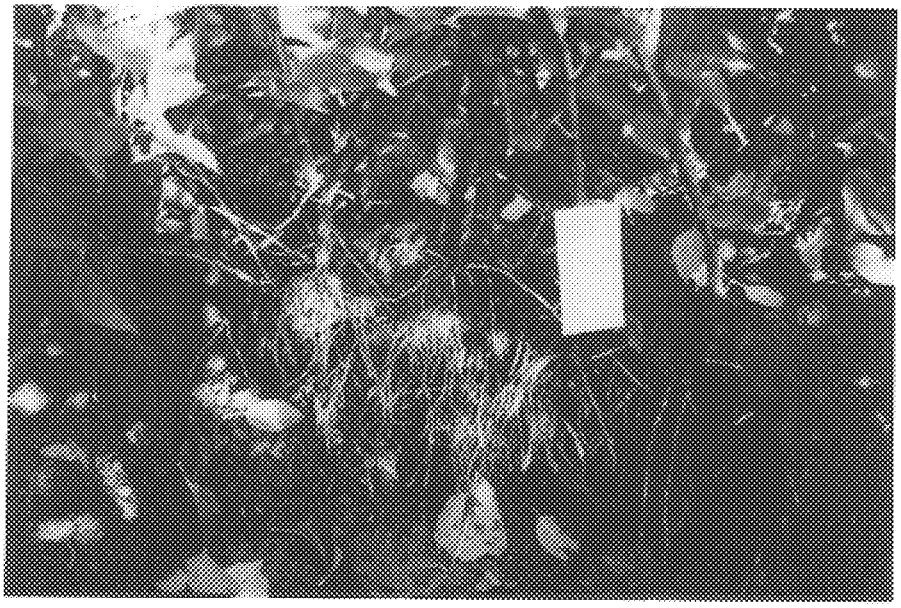
FIG. 4 shows the typical root growth following five months in the stoolbed.
Figure 5:
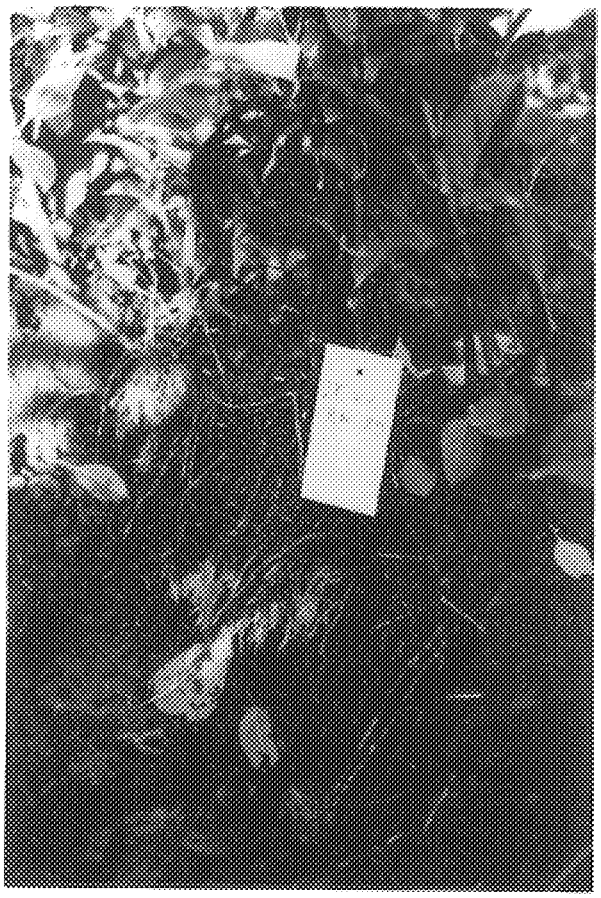
FIG. 5 shows root quality and quantity on rootstocks in the stoolbed.
Figure 6:
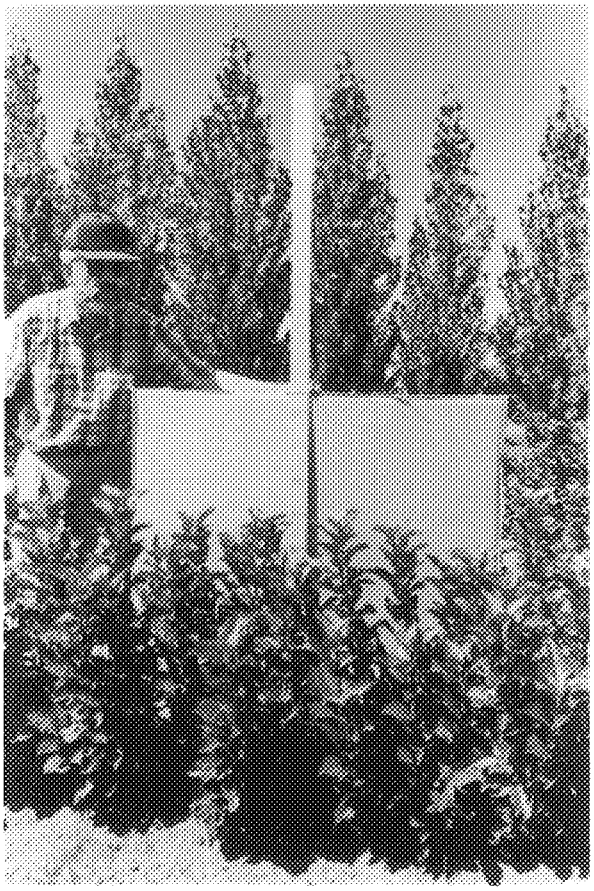
FIG. 6 shows the average height in centimeters of M 9 rootstock daughter plants in a stoolbed row in Ephrata, Wash.
Figure 7:
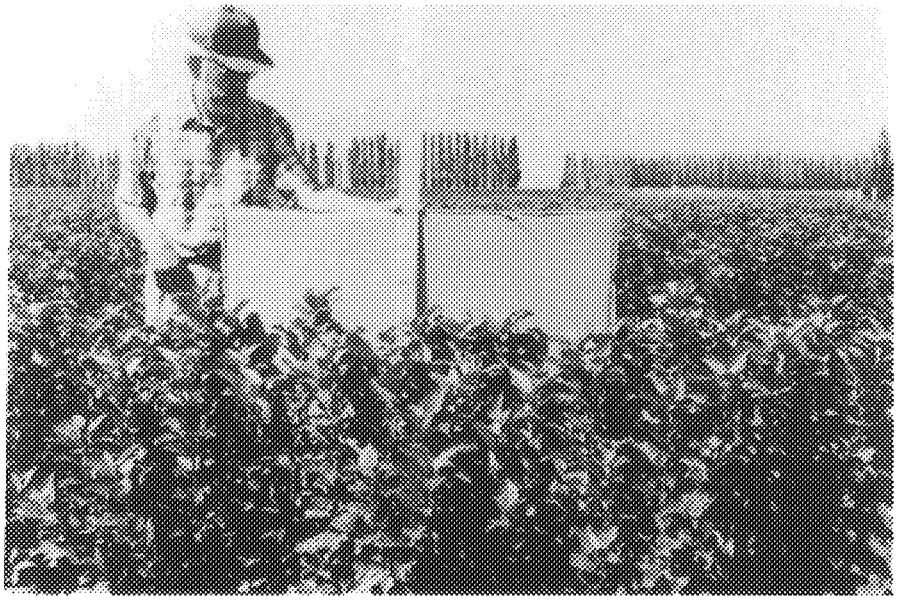
FIG. 7 shows the average height in centimeters of RN19 rootstock daughter plants in a stoolbed row in Ephrata, Wash.

The following is a detailed description of the new apple rootstocks growth characteristics based on the stoolbed plants grown at the six test sites described above. Colors of the leaves and shoots are based on their appearance at the sites where grown. In those instances where a precise color assessment can be made, reference is to the Munsell Limit Color Cascade Table. In other instances, general color terms are used in accordance with the ordinary dictionary significance.

General habit:
- *Strength of growth*.—Vigorous, stiff.
- *Habit*.—Upright.
- *Branching*.—Few, flexible.

Vegetative Shoots:
- *Bark color*.—Greenish-brown (21-14).
- *Pubescence*.—Finely tomentose.
- *Lenticels*.—Few, inconspicuous, widely spaced, small, white.

Leaves:
- *Size*.—6 cm wide, 9.1 cm long.
- *Shape*.—Broad elliptic, slightly asymmetric.
- *Base*.—Obtuse, attenuated.
- *Apex*.Macronate, acutely tipped.
- *Serrations*.—Sinuate at sides, obtuse at base.
- *Spacing*.—Normal phyllotaxical arrangement for Malus.
- *Color*.—Yellow-green (22-13) with pinkish tips.

*Leaf scars:*
- *Shape*.—Broad V, slightly raised.
- *Color*.—Dark brown.

Petioles:
- Shape.—Blender, slightly channeled.
- Length.—Medium, 3.1 cm.
- Color.—Reddish-brown (32-12).
- Pose.—Acute angle near tip, mostly horizontal along sides.
- Glands.—None.

Stipules:
- Size.—Small, 4 mm, inconspicuous, minutely serrated.
- Color.—Greenish yellow.
- Pose.—Mostly reposed along petiole.

Lateral buds:
- *Size*.—Small.
- *Shape*.—Flat, angular.
- *Color*.—Dark brown.
- *Pubescence*.—Finely tomentose.

Apical Buds;
- *Size*.—Small.
- *Shape*.—Flat, angular.
- *Color*.—Dark brown.
- *Pubescence*.—Finely tomentose.

Dormant Plant

Shoots:
- *Size*.—Stocky, 6–11 mm in caliper at base, stiff, brittle.
- *Bark color*.—Dark brown (25-15).
- *Pubescence*.—Conspicuously pubescent.

*Nodes*.—Larger in diameter than internodes with slight shoulder at each side on leaf scar.

*Internodes*.—Smooth, regularly spaced.

Stooling and root characteristics

Rooting and stooling: Multiplies well in stoolbeds, forming strong roots along full length of shank. Roots arise from nodes.

Habit of growth in stoolbed: Shoots arise from nodes, grow mostly outward at a slight angle.

Flower characteristics

Flowers:

*Size*.—3.6 cm in diameter.

*Color*.—White with pink streaks at base.

Fruit: (No commercial value, but useful for identification).

*Shape*.—Round to slightly oblong.

*Color*.—Red Stripes.

*Size*.—About 4.5 cm in diameter and about 5.5 cm in length.

*Flavor*.—Bland, tasteless.

General Characteristics

Rootsuckering: Few rootsuckers.

Size control potential: Size of trees budded on the subject rootstocks will vary according to the vigor of the cultivar and/or type of soil and orchard management. "Standard" growing cultivars such as Red and Golden Delicious are reduced in size about 65% when compared to trees on apple seedling rootstocks. Less vigorous varieties are more reduced in size and more vigorous varieties are less reduced in size.

Dwarfing: Fully dwarfing.

Precocity: Varies according to variety, most cultivars often flower and set fruit the first year in the orchard and thereafter bear fruit each year.

Compatiblity: Graft compatible with all major commercial fruiting varieties.

Root anchorage: Needs support.

Hardiness: Hardy in most commercial apple growing areas.

Disease and pest resistance: Average resistance to common diseases and pests of apple. Tested and found free of all known viruses and virus-like diseases of apple.

What is claimed is:

1. A new and distinct apple tree clone, a sport of the Malling 9, referred to by the cultivar designation 'M9-RN19', substantially as herein shown and described, characterized particularly by its stability to serve as a rootstock for grafting of apple tree cultivars to produce dwarf apple trees and by its ability to root very readily in the stoolbed with very little lateral branching and produce high quality stoolbed rootstock plants for nursery use.

* * * * *